United States Patent
Garth et al.

(10) Patent No.: US 8,372,023 B2
(45) Date of Patent: Feb. 12, 2013

(54) HIGHLY ADJUSTABLE LUMBAR BRACE

(76) Inventors: Geoffrey Garth, Long Beach, CA (US); Steven Burke, Huntington Beach, CA (US); Albert Romo, Lakewood, CA (US); Joel Perez, Long Beach, CA (US)

( * ) Notice: Subject to any disclaimer, the term of this patent is extended or adjusted under 35 U.S.C. 154(b) by 0 days.

(21) Appl. No.: 13/036,340

(22) Filed: Feb. 28, 2011

(65) Prior Publication Data
US 2011/0213284 A1 Sep. 1, 2011

Related U.S. Application Data

(60) Provisional application No. 61/308,728, filed on Feb. 26, 2010.

(51) Int. Cl.
A61F 5/00 (2006.01)
A61F 5/37 (2006.01)

(52) U.S. Cl. .......................... 602/19; 128/876

(58) Field of Classification Search .............. 602/5, 6, 602/12, 16, 19; 128/99.1, 96.1, 102.1, 100.1, 128/101.1; 2/467, 465, 44, 311, 312, 321, 2/322; D24/190
See application file for complete search history.

(56) References Cited

U.S. PATENT DOCUMENTS

| | | | |
|---|---|---|---|
| 2,036,484 A * | 4/1936 | Le May | 450/119 |
| 2,100,964 A * | 11/1937 | Kendrick | 602/19 |
| 2,117,309 A * | 5/1938 | Fritsch | 602/19 |
| 4,080,962 A * | 3/1978 | Berkeley | 602/19 |
| 5,346,461 A | 9/1994 | Heinz et al. | |
| 5,433,697 A * | 7/1995 | Cox | 602/19 |
| 5,437,617 A | 8/1995 | Heinz et al. | |
| RE35,940 E | 10/1998 | Heinz et al. | |
| 6,102,879 A | 8/2000 | Christensen | |
| 6,190,343 B1 | 2/2001 | Heinz et al. | |
| 6,213,968 B1 | 4/2001 | Heinz et al. | |
| 6,503,215 B1 | 1/2003 | Reinhardt et al. | |
| 6,517,502 B2 * | 2/2003 | Heyman et al. | 602/5 |
| 6,602,214 B2 | 8/2003 | Heinz et al. | |
| 6,676,620 B2 * | 1/2004 | Schwenn et al. | 602/12 |
| 6,964,644 B1 * | 11/2005 | Garth | 602/19 |
| 7,118,543 B2 * | 10/2006 | Telles et al. | 602/19 |
| 7,186,229 B2 | 3/2007 | Schwenn et al. | |
| 7,201,727 B2 * | 4/2007 | Schwenn et al. | 602/12 |
| 2001/0020144 A1 | 9/2001 | Heinz et al. | |
| 2001/0034498 A1 | 10/2001 | Heyman et al. | |
| 2005/0251074 A1 | 11/2005 | Latham | |
| 2005/0267390 A1 * | 12/2005 | Garth et al. | 602/19 |
| 2005/0273025 A1 | 12/2005 | Houser | |
| 2006/0004313 A1 | 1/2006 | Heinz et al. | |
| 2009/0082707 A1 | 3/2009 | Rumsey | |
| 2009/0192425 A1 * | 7/2009 | Garth et al. | 602/19 |
| 2009/0204042 A1 * | 8/2009 | Park | 602/19 |
| 2010/0217167 A1 * | 8/2010 | Ingimundarson et al. | 602/19 |

FOREIGN PATENT DOCUMENTS

FR 2682869 A1 * 4/1993

* cited by examiner

*Primary Examiner* — Nicholas Lucchesi
*Assistant Examiner* — Kari Petrik
(74) *Attorney, Agent, or Firm* — Fish & Associates, PC

(57) ABSTRACT

A back brace is designed to custom fit a wearer in a multitude of different configurations. First, the back brace could have a lumbar support that is split into upper and lower sections that are connected to a flexible joint, allowing the lumbar support to bend towards the spine of the user. The lumbar support is also generally split into left and right sections that are drawn towards one another while the joint bends towards the lumbar curve, This allows the back brace to conform to the lumbar curve of the wearer as a custom fit. Second, the brace could have optional extenders that alter the support length, width, and height of lumbar and lateral supports about the wearer. Third, the brace could have reinforcement support mechanisms that alter the rigidity of various lumbar and lateral supports about the wearer.

15 Claims, 8 Drawing Sheets

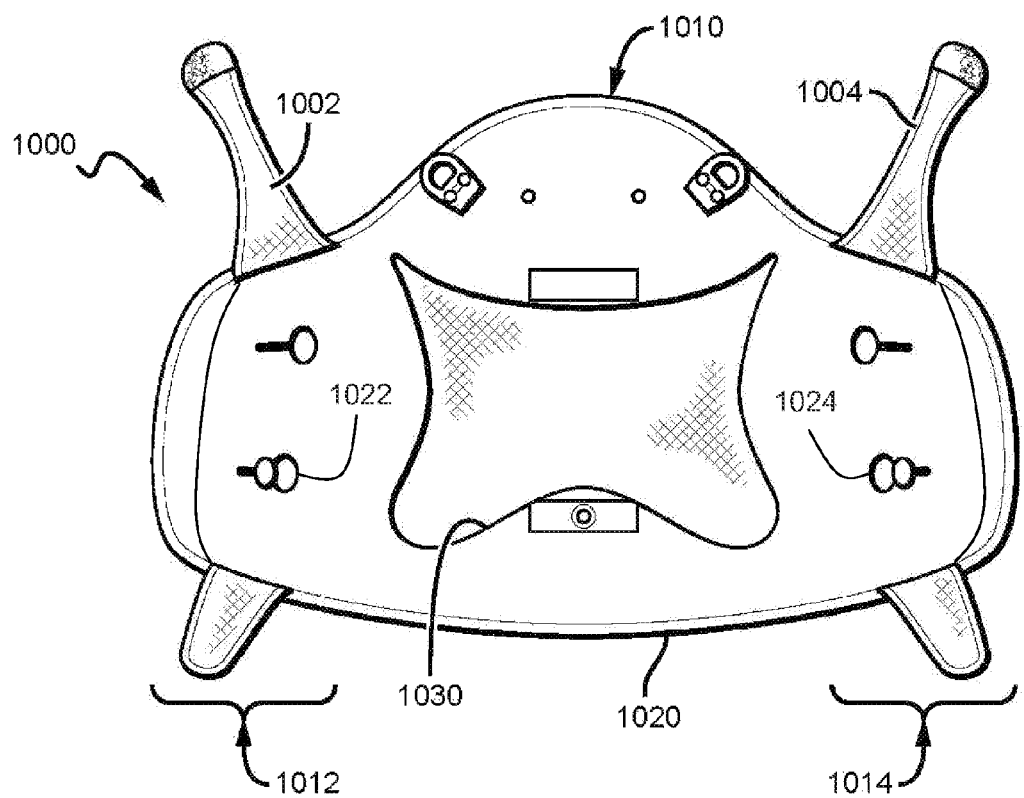
FIG. 9
FIG. 10
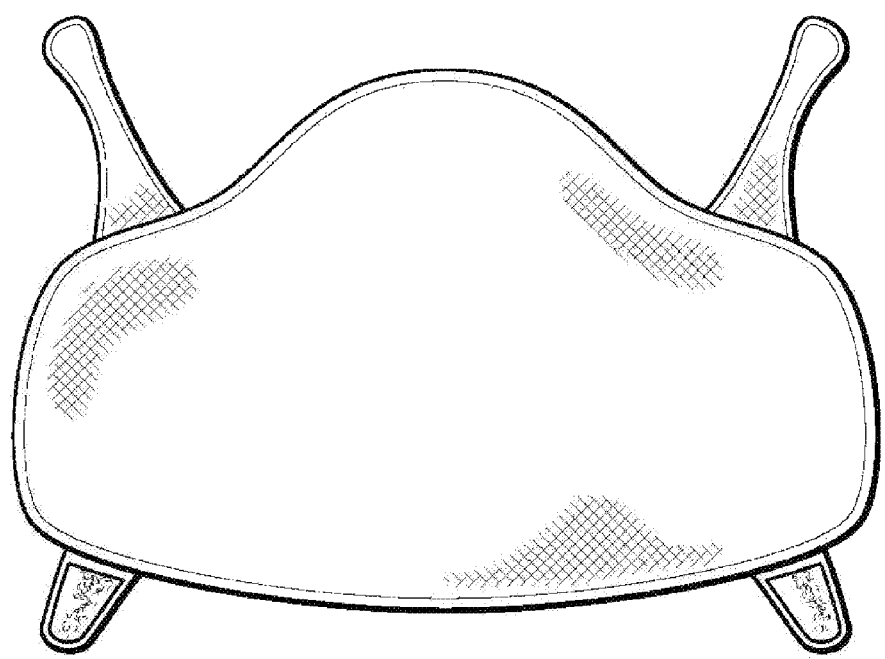

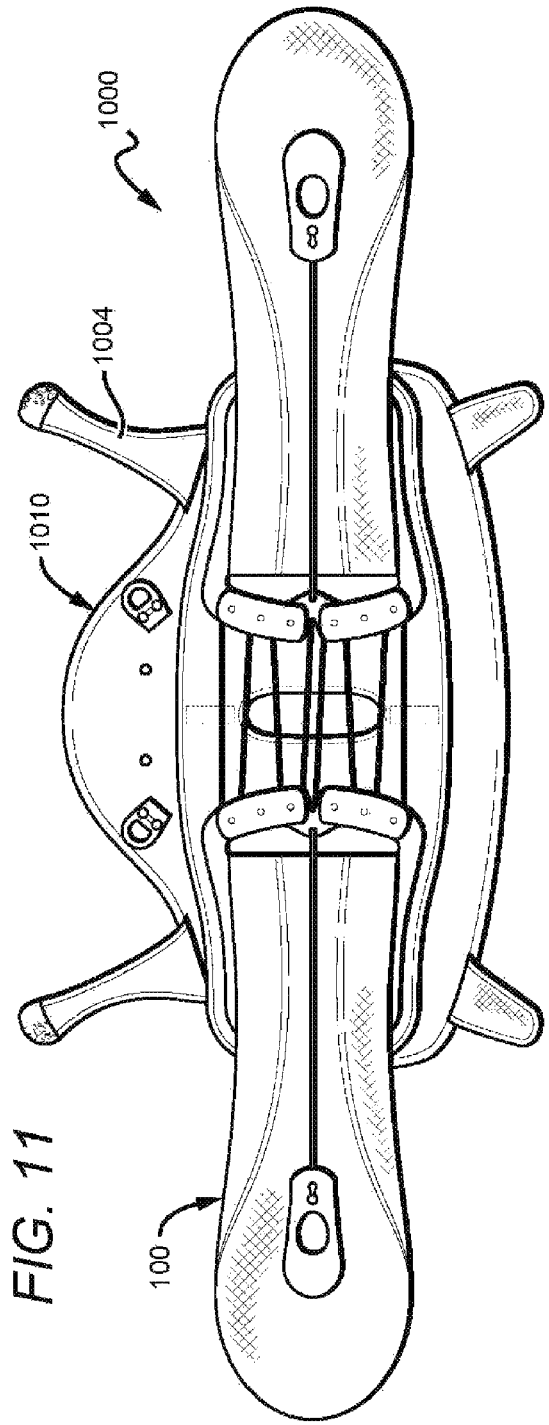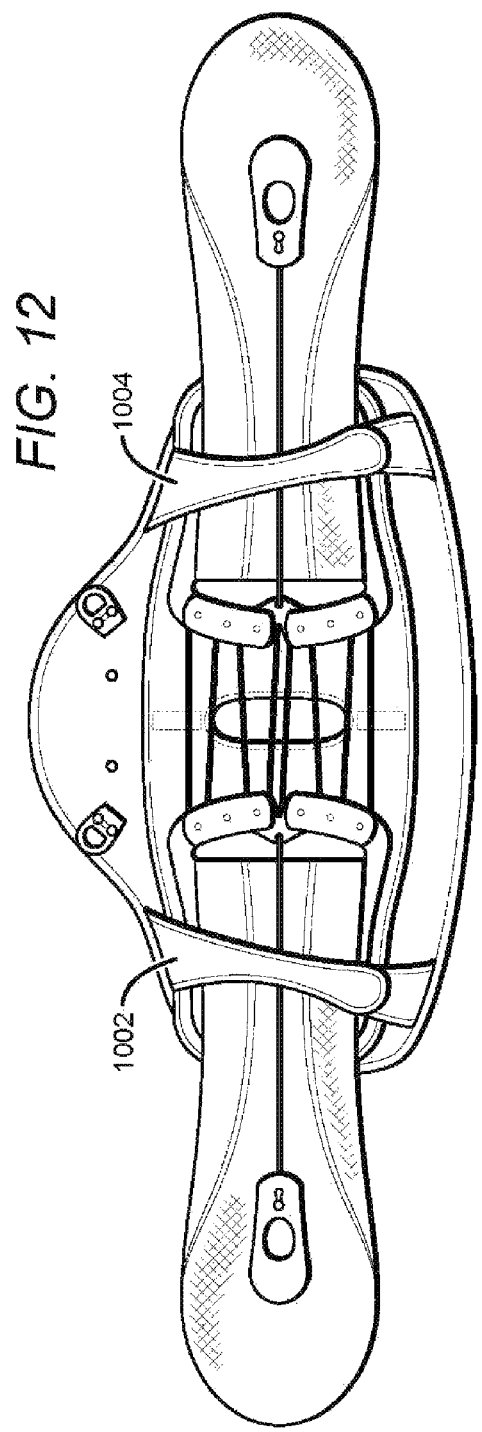

HIGHLY ADJUSTABLE LUMBAR BRACE

This application claims priority to 61/308728, filed Feb. 26, 2010. All extrinsic materials identified herein are incorporated by reference in their entirety.

FIELD OF THE INVENTION

The field of the invention is wearable lumbar supports.

BACKGROUND

Orthotic devices are typically provided for partial or substantial immobilization of the torso to stabilize the back. Some orthotic devices are back braces that fit around the torso around the lumbar area. When worn properly, a body brace can lend additional support to the abdomen and the spinal column to achieve spinal stability. However, for many users body braces are difficult to appropriately position and fasten. For example, U.S. Pat. No. 4,640,269 to Goins provides a back brace that is tightened around the body by threading a Velcro strap through a loop and pulling the strap backwards towards the user's posterior. The awkward angle of the strap prevents users from fully tightening the strap themselves and requires a third party to assist in the tightening process.

Goins and all other extrinsic materials identified herein are incorporated by reference in their entirety. Where a definition or use of a term in an incorporated reference is inconsistent or contrary to the definition of that term provided herein, the definition of that term provided herein applies and the definition of that term in the reference does not apply.

US 2007/0017945 to Willis teaches a body brace that wraps around a user's lumbar region and has a belt with a strap that pulls forward to fit the brace around the user. Willis' body brace is easier to tighten since the strap tightens by pulling forward, which is a natural body movement. Willis, however, fails to contour to body shapes of different shapes and sizes, for example differently shaped hips and different lordotic curves.

U.S. Pat. No. 6,213,968 to Heinz teaches a custom fitted orthotic device with cables with a split lumbar support that is tightened around a lumbar region using pulleys and cords. Heinz, however, provides either rigid support or flexible support, and fails to allow the lumbar support to flex and bend into the lumbar curve while the lateral support remains rigid. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It has yet to be appreciated that stiff lumbar supports could have flexible joints that wrap around a patient's curvature to provide a stiff support that is custom fit.

Thus, there is still a need in the art for a body brace that conforms to body shapes of different shapes and sizes.

SUMMARY OF THE INVENTION

The present invention provides apparatus, systems, and methods in which one could use a brace to support the lumbar region of a patient by providing a lumbar support having a joint between upper and lower sections of the lumbar support. The upper and lower sections of the lumbar support are generally rigid with respect to the joint such that the joint can move anteriorly relative to the coronal plane of the body such that the joint folds into the curve of the lumbar region and the upper and lower sections "hug" the lumbar region. As used herein, the term "rigid" refers to a material that will not fold in half without permanently deforming the shape of the material, such as by snapping or breaking. A rigid material may bend slightly under pressure and return to its previous form when such pressure is removed, but will not fold in half. Contrast this with a "flexible" material, which could be unfolded to a planar form and could be folded in half with ease, without permanently deforming the shape of the material.

The upper and lower sections of the lumbar regions preferably have right and left sections that are coupled together by upper and lower mechanically advantaged systems. Contemplated mechanically advantaged systems include series of pulleys, gears, levers, screws, or combinations thereof that provide force to an adjustment mechanism. Preferably, the advantaged adjustment mechanism is mechanically advantaged more than 2:1, and is more preferably mechanically advantaged at 4:1 or more. Additional pulleys or longer levers could easily increase the mechanical advantage ratio of the mechanism. Exemplary mechanically advantaged systems are further described in co-pending U.S. application Ser. Nos. 12/394,867, 10/977,726, and 10/440,525, which are each incorporated herein by reference.

An exemplary mechanically advantaged system includes pulleys and cords that work to draw the left and right sections of the support region towards one another, towards the front/anterior side of the wearer. Such pulley systems could have 2, 3, 4, 5, or more pulleys, depending on the size and strength needed in such a device. In order to prevent the right and left sections of the lumbar support from pulling too far apart from one another, a limiter is preferably provided that prevents the left and right sections from moving a threshold distance away from one another. For example, a limiter could be a cloth, rope, or other material that couples the right and left sections without stretching. The limiter is preferably made from a compressible material to allow the right and left sections to fold over one another during storage, and also preferably includes a hole along the sagittal midplane of the wearer to allow a doctor to access the lumbar region of the wearer without removing the brace itself.

One or more optional extenders could be coupled with the lumbar support to extend the effective length, width, or height of the lumbar support, allowing for greater flexibility in the form and function of the brace. The optional extenders could alter the length, width, or height of the lumbar support by a variety of lengths, for example at least 2 inches, 5 inches, 10, inches, or 15 inches. Multiple extenders could be configured to attach to one another, allowing for a variety of extension configurations for wearers of different sizes and/or needs. Rigid reinforcing supports could also be coupled to the lumbar support, overlapping the joint, to prevent the flexible joint from bending in certain configurations.

The body brace preferably also has a rigid lateral support that reinforces the wearer's oblique muscles. Preferably, the rigid lateral support has a surface area greater than 4, 5, 10, 15, or 20 square inches. In an exemplary embodiment, the rigid lateral support extends anteriorly past a midline of the wearer. The lateral support may have an optional extender that couples to the lateral support to extend an effective length, width, or height of the lateral support, and/or may overlap with sections of the lateral support to reinforce a rigidity of the lateral support. Such optional extenders could alter the length, width, or height of the lumbar support by a variety of lengths, for example at least 2 inches, 5 inches, 10, inches, or 15 inches. Multiple extenders may be attached to one another to extend the lateral support for a plurality of lengths, or to reinforce the lateral support for a plurality of rigidity strengths.

The present invention provides apparatus, systems and methods in which a body brace is configured to conform and fit a variety of body shapes of different shapes and sizes.

BRIEF DESCRIPTION OF THE DRAWING

FIG. 9 is a rear plan view of an embodiment of an extender.

FIG. 10 is a front plan view of an embodiment of the extender of FIG. 9.

FIG. 11 is a rear plan view of the quick draw brace of FIG. 7 juxtaposed with the extender of FIG. 9.

FIG. 12 is a rear plan view of the quick draw brace of FIG. 7 with the extender of FIG. 9 attached to the quick draw brace.

DETAILED DESCRIPTION

Figure 1:
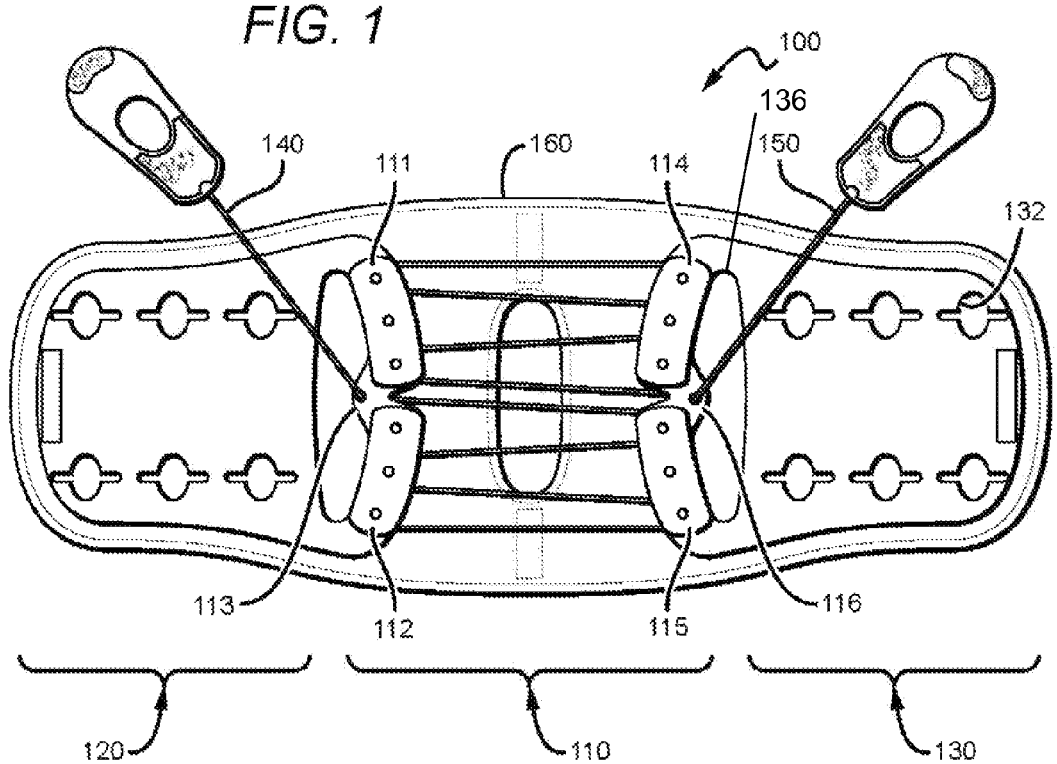
FIG. 1 is a rear plan view of an embodiment of a quick draw brace.
Figure 2:
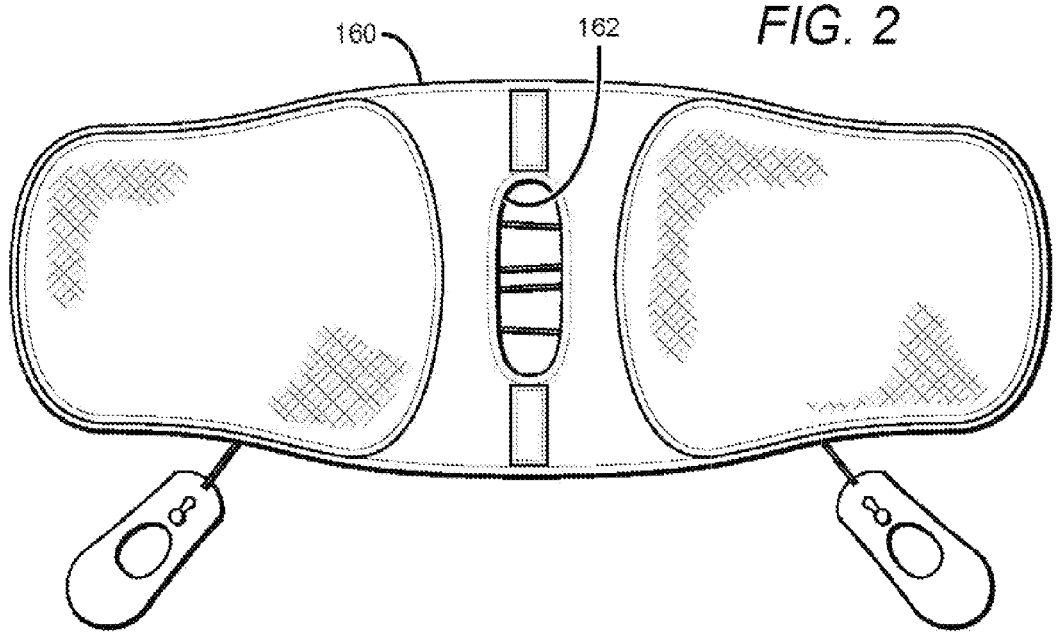
FIG. 2 is a front plan view of the quick draw brace of FIG. 1.

FIGS. 1 and 2 show a quick draw brace 100 with a lumbar support 110, lateral supports 120 and 130, cords 140 and 150, and limiter 160. Lumbar support 110 is split into upper left section 111, lower left section 112, upper right section 114, and lower right section 115. Upper left section 111 and lower left section 112 are configured to pivot with respect to one another along flexible joint 113, and likewise upper right section 114 and lower right section 115 are configured to pivot with respect to one another along, flexible joint 116.

Upper left section 111, lower left section 112, upper right section 114, and lower right section 115 are all preferably rigid or semi-rigid in order to provide support to the upper lumbar curve and the lower lumbar curve of the wearer.

Lateral supports 120 and 130 are preferably made of a semi-rigid or rigid material to provide lateral support to a user. While the current embodiment shows lateral support 120 being wholly contiguous with left lumbar support sections 111 and 112, the lateral support could be made separately from the lumbar supports without departing from the scope of the current invention. It is preferred that the lateral support is a semi-rigid material that is greater than 4 or 5 inches so that the lateral support would pass the midline of the wearer.

Figure 8:
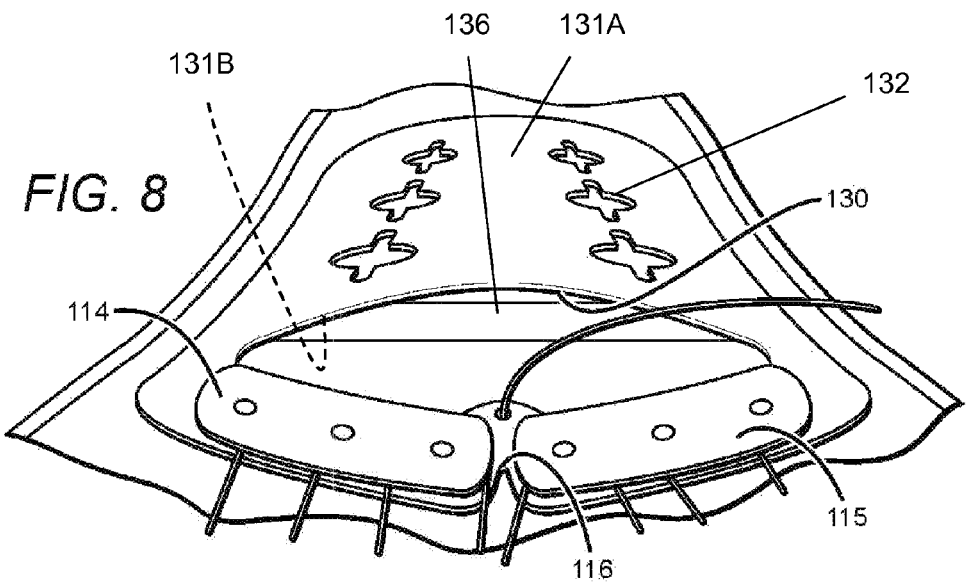
FIG. 8 is a perspective view of the brace of FIG. 1 with the lumbar support in a bent position.

In the current embodiment, flexible joints 113 and 116 are created by creating a thin peninsula of a substantially rigid plastic polymer separate from the lateral supports 120 and 130. Since the peninsula is so thin (approximately 1.5 centimeters across), the upper and lower sections are able to bend along the joint, whereas they would not be able to if the peninsula was much wider. As shown in FIG. 8, as the upper and lower sections bend inward, the lateral section does not also bow inward because of the shape of the peninsula. In reality, lateral section 130 bows outward slightly, which is largely contained when cord 150 is pulled against lateral section 130. One skilled in the art would understand that other flexible joints could be used, for example by using a cloth lumbar support or by adding a hinge or series of hinges to a more rigid peninsula.

Cords 140 and 150 are attached to pulleys (shown in FIGS. 18 and 19) in the upper and lower sections in a similar manner to the pulleys described in US2009/0192425 and U.S. Pat. No. 7,001,348. This creates a mechanically advantaged system such that when a wearer pulls cords 140 and 150, these sections could then fold anteriorly until the flexible joint engages the lordotic curve of the wearer's posterior side, allowing for a tighter fit. Since the lateral supports 120 and 130 are coupled to the lumbar support 110 via thin, semi-rigid peninsulas, the lateral supports do not bend when the cords are pulled. Preferably, the pulley system comprises an elastic band or spring that will automatically retract the cord when a force ceases to be applied to the cord.

Cords 140 and 150 terminate in handles 142 and 152, which each have hook and loop attachments that could be attached to left and right adjustment mechanisms 310 and 320 shown in FIGS. 3-8. Left adjustment mechanism 310 and right adjustment mechanism 320 preferably both have loop material along a majority of their lengths along the front side, to allow cord handles 142 and 152 to be attached to any portion of the adjustment mechanism. Right adjustment mechanism 320 also has hook attachments along its tip to allow it to mate with the front side of left adjustment mechanism 310 when wrapped around a wearer.

Limiter 160 is an underlying cloth that lumbar support 110 is attached to. Since limiter 160 is made of a substantially inelastic material, limiter 160 prevents cords 140 and 150 from being pulled too far towards the holes, effectively controlling the minimum distance that the cords can be retracted. As used herein, a 5 inches (12.7 cm) of a "substantially inelastic material" does not stretch more than 3 mm without tearing. Limiter 160 also has hole 162, which allows access to the lumbar region of the wearer for emergencies, and also prevents direct force from being applied to the lumbar region in case of severe injury.

Figure 3:
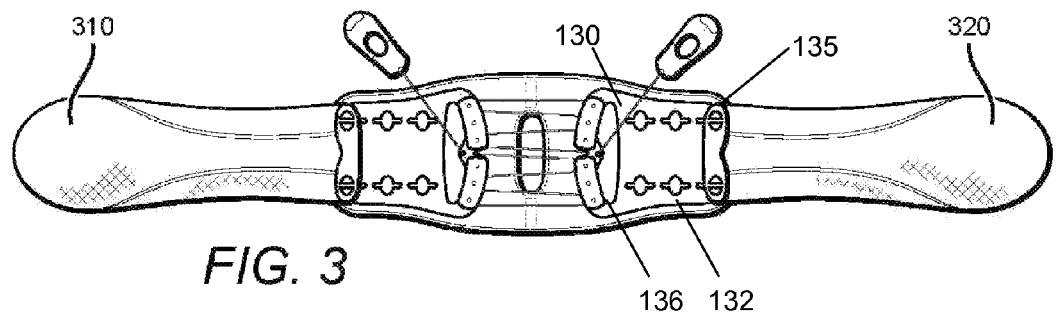
FIG. 3 is a rear plan view of the quick draw brace of FIG. 1, with fitting belts attached to the rear side of the lateral support.
Figure 4:
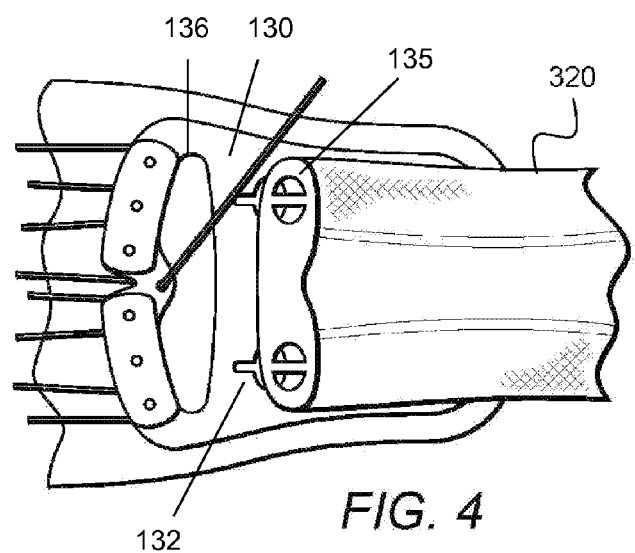
FIG. 4 is an exploded view of the quick draw brace of FIG. 3.
Figure 5:
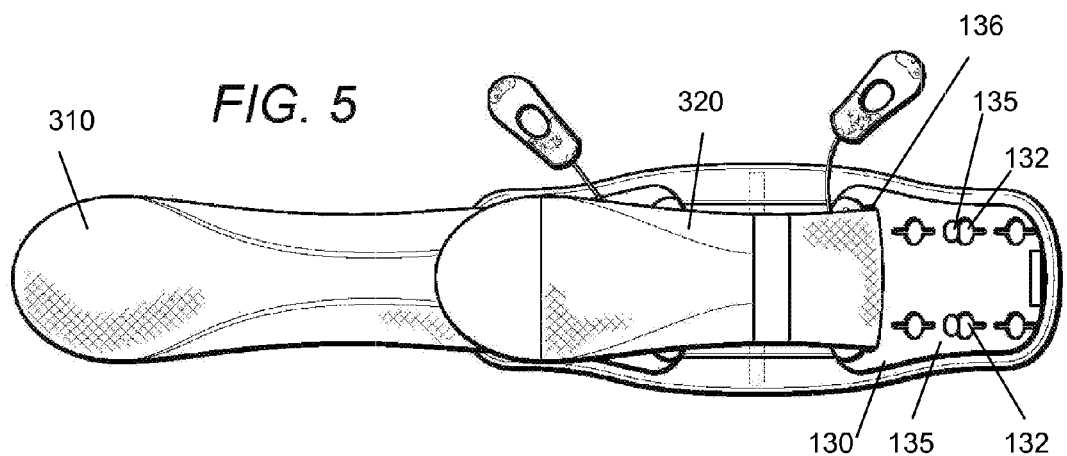
FIG. 5 is a plan, rear view of the quick draw brace of FIG. 1, with fitting belts attached to the front side of the lateral support.
Figure 6:
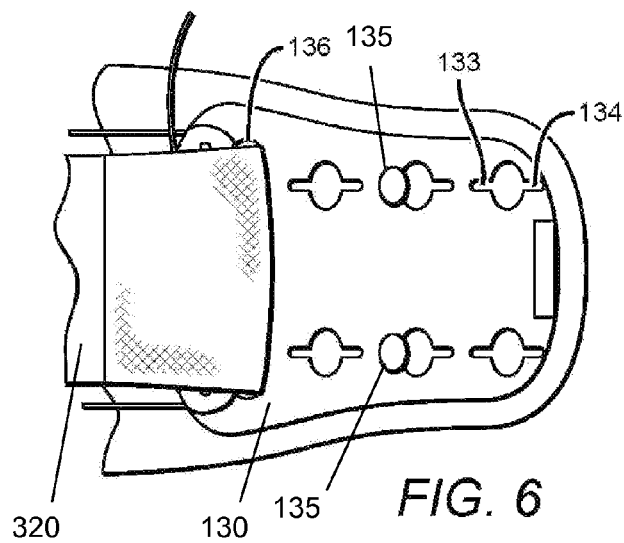
FIG. 6 is an exploded view of the quick draw brace of FIG. 5.
Figure 7:
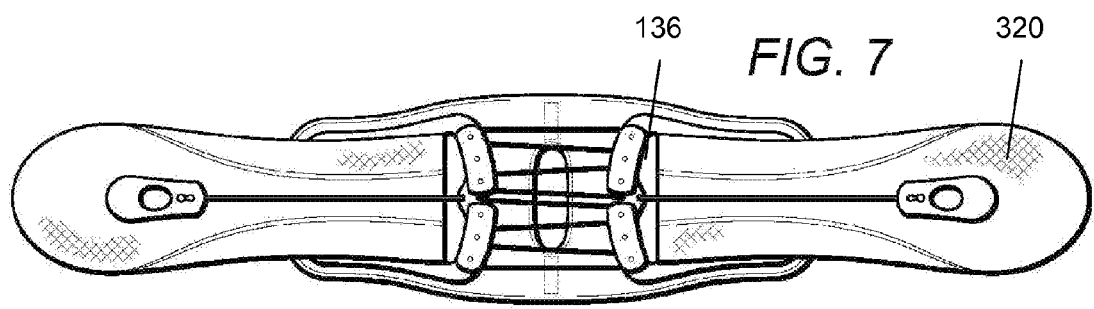
FIG. 7 is a plan view of the quick draw brace of FIG. 6, with the fitting belt folded over.

Right adjustment mechanism 320 attaches to lateral support 130 via holes 132. As shown in FIG. 6, hole 132 comprises two opposing bolt recesses 133 and 134. This allows right adjustment mechanism to attach to a front side of lateral support 130 as shown in FIGS. 3 and 4, or attach to the rear side of the lateral support 130 as shown in FIGS. 5 and 6. Allowing right adjustment mechanism 320 to attach to either the front or a rear side of the lateral support 130 doubles the adjustment length as compared to an adjustment mechanism that merely attaches to one side of the lateral support 130. It is contemplated that other methods of attaching adjustment mechanisms 310 and 320 to the lateral supports could be used, for example buttons, claps, hooks, or even more hook and loop attachments.

As shown in FIGS. 5 and 6, when right adjustment mechanism 320 attaches to the rear side of the lateral support 130 using connectors 135, the adjustment mechanism 320 needs to thread through loophole 136 in order to be orientated correctly for wearing. Loophole 136 is shown as a hole in lateral support 130, but could be a recess (or an open hole) without departing from the scope of the invention. Since right adjustment mechanism 320 could attach to either a front side 131A or a rear side 131B of the lateral support 130 (shown best in FIG. 8), the length of right adjustment mechanism 320 could be altered considerably. Additionally, shorter or longer adjustment mechanisms could be provided to allow an even greater variability in sizes. The holes 132 could also be used to attach other lateral supports to accommodate larger wearers and extend the length even further.

Figure 13:
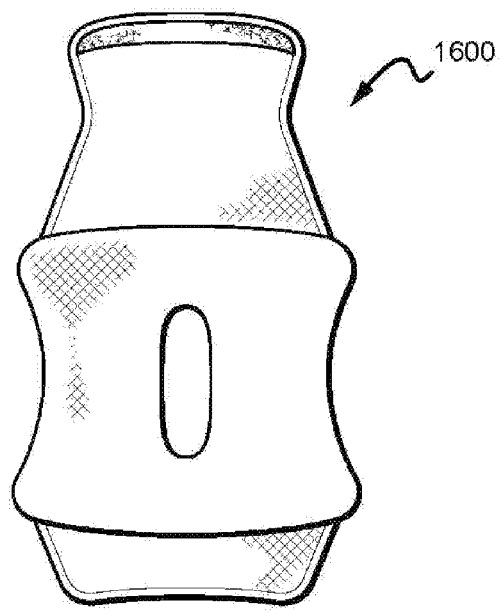
FIG. 13 is a rear plan view of a reinforcement panel.
Figure 14:
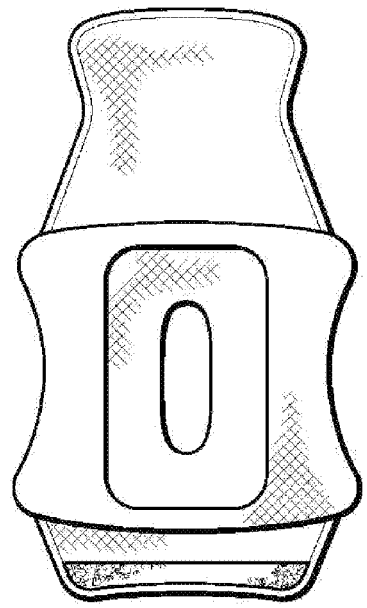
FIG. 14 is a front plan view of the reinforcement panel of FIG. 13.

The effective height and width of lumbar support 110 could be extended using extender 1000 with optional rigid support 1010 and padding 1020, shown in FIGS. 10 and 11. Rigid support 1010 preferably overlaps with some of the surface of lumbar support 110 to reinforce the rigidity of lumbar support 110. While the drawing illustrates that padding 1020 covers hole 1030, it is preferred that padding 1020 has a hole that matches hole 1030, preventing any padding from touching the delicate spinal column along the lumbar region, and providing access to the lumbar region. When lumbar support 110 is attached to extender 1000 as shown in FIGS. 12 and 13, the effective height of the lumbar support and the effective lengths of the lateral supports could be lengthened considerably.

Preferably, the effective height of the lumbar support is lengthened so that the lumbar support provides support from the sacrococcygeal junction to the 9th thoracic vertebra. This effective height is generally greater than 9 inches in an average adult, and may extend more than 10, 11, 12, 13, or 14 inches, depending on the size of the user. In another embodiment, the effective height of the lumbar support could be adjusted by attaching or detaching other extendable support structures.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

The effective length that is added by extender 1000 could be further altered by removing lateral extenders 1012 and 1014, or by replacing the lateral extenders with longer or differently shaped extenders. As shown in FIG. 9, lateral extenders 1012 and 1014 mate with bolt holes 1022 and 1024, respectively, and overlap with a portion of the rigid support 1010 to reinforce the strength of a portion of the rigid support 1010. The rigid support 1010 shown as being constructed from three separate panels—a mid-panel, a left lateral extender 1012, and a right lateral extender 1014—the rigid support could be made from more or less portions as needed. Preferably, the rigid support 1010 is made from the same material as lateral supports 120 and 130, but could be made from different material if needed.

Figure 15:
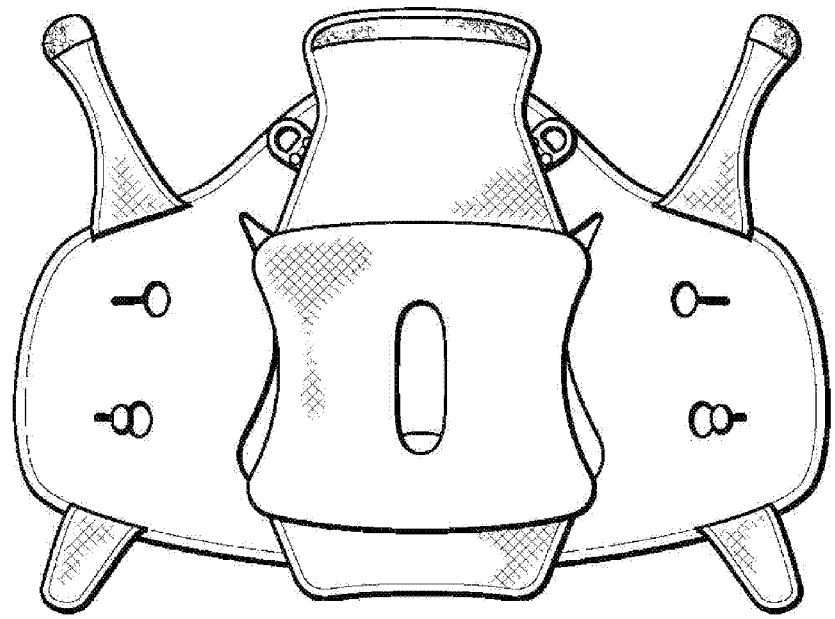
FIG. 15 is a rear plan view of the extender of FIG. 9 juxtaposed with the reinforcement panel of FIG. 13.
Figure 16:
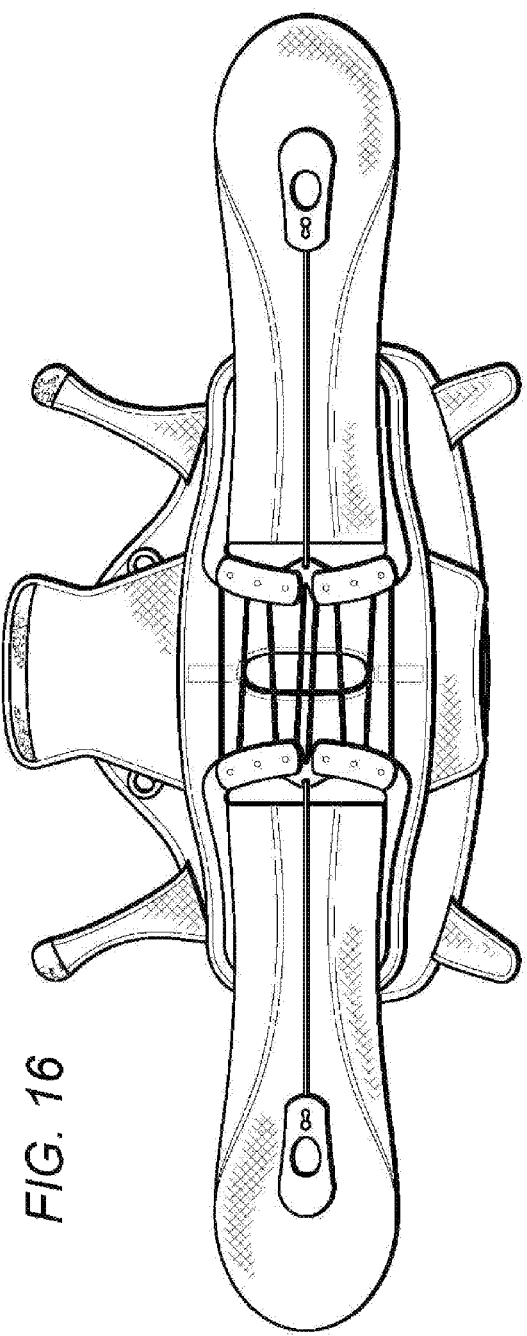
FIG. 16 is a rear plan view of the extender and reinforcement panel of FIG. 15 juxtaposed with the quick draw brace of FIG. 7.
Figure 17:
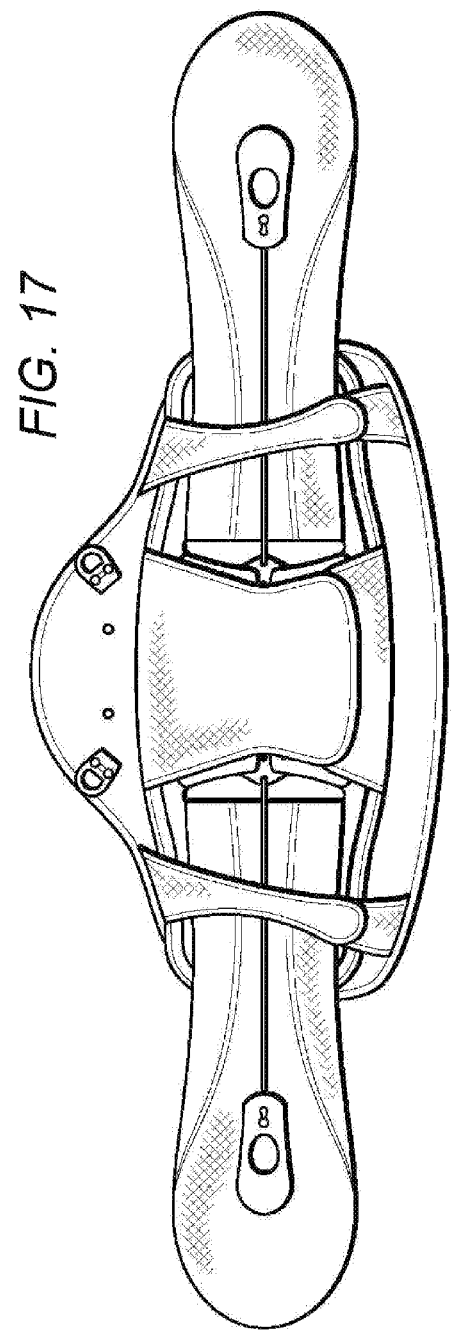
FIG. 17 is a rear plan view of the extender, reinforcement panel, and quick draw brace of FIG. 16 coupled with one another.

FIGS. 15 and 16 show the front and back portions of detachable small back panel 1600. Small back panel 1600 is preferably made from a rigid material covered in padding to protect the regions close to the spine. As shown in FIGS. 13-17, the small back panel could be wrapped around lumbar support 110 to prevent lumbar support 110 from bending into the lumbar curve of the wearer and to add a more rigid support structure to the lumbar region.

Figure 18:
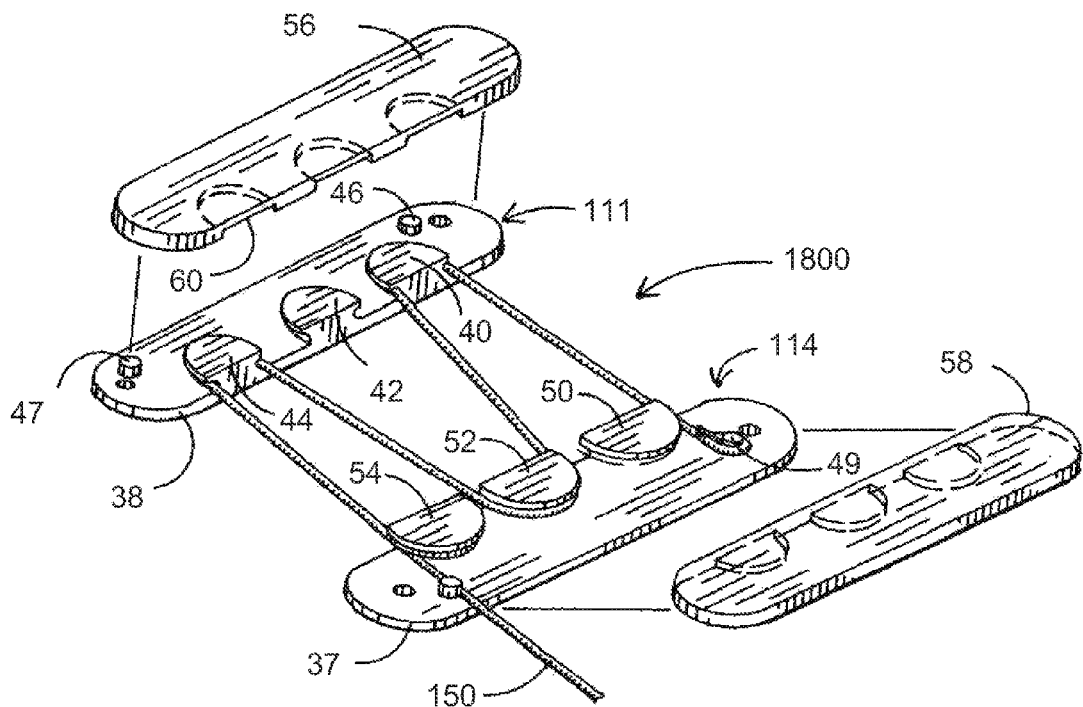
FIG. 18 is an enlarged, exploded view, showing the cord guide parts within the upper left and right sections of the brace of FIG. 1.
Figure 19:
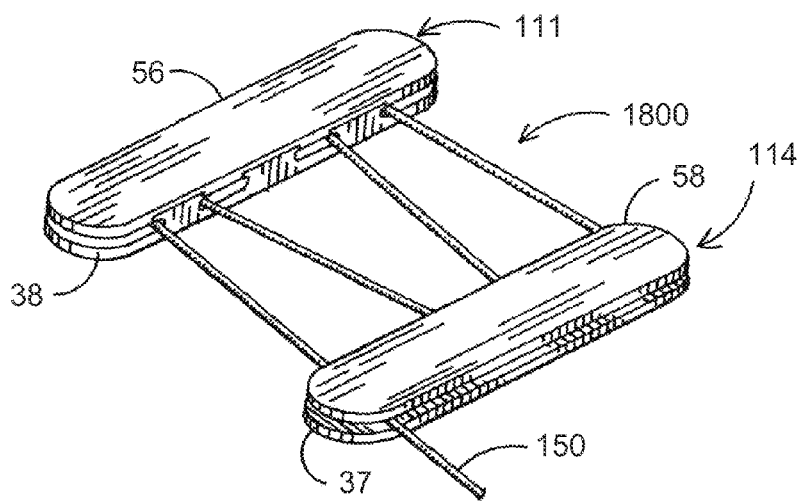
FIG. 19 is a perspective view of the upper left and right sections of FIG. 18 in the assembled configuration.

FIGS. 18 and 19 show the configuration of a mechanically advantaged system 1800 represented as upper left section 111 and upper right section 114, which are pulled together using cord 150. The lower left and lower right sections are constructed in the same manner. The upper left section 111 has an upper left cord guide base 38, which has three pulleys, shown in the figure as cord guide lobes 40, 42, and 44 thereon. In addition, the base 38 has posts 46 and 47 which snap into matching detents (not shown) in cap 56. The cord guide lobes 40, 42, and 44 are half round and are undercut on their half circumference. The under cut is circular in profile and is at least as large as the diameter of the cord. The under cuts are preferably smooth so that cord 150 can be engaged therearound and smoothly moved around the lobes. For smooth movement, it is preferably that the upper left section 111 and upper right section 114 be made of a low friction polymer, such as nylon or Teflon. The upper right section 114 is similar to upper left section 111, and also has three cord guide lobes 50, 52, and 54 on its base 37, which act as pulleys for cord 150. The cord 150 has an eye thereon engaged over post 49 on cord guide 114. The cord 150 engages around love 40, lobe 52, and thence lobe 44 to extend out over the base 37. When the cord 150 is pulled, the upper left section 111 and upper right section 114 are pulled together with a 4-to-1 mechanical advantage (neglecting friction) The cord 150 is preferably a strong cord with low friction characteristics with respect to the cord guide lobes, such as nylon.

In order to hold a cord in place on the lobes, caps 56 and 58 could be used to cover the bases 38 and 37, respectively. The caps have half round recesses 60 that engage over the lobes. The recess 60 engages over lobe 44 to hold the cord in the undercut below the top of lobe 44, and hold the cord loop on the post 49. The caps can be attached in any other suitable way, for example by using adhesives or mating buttons. Other pulley mechanisms are contemplated, for example pulleys mounted on wheels.

Thus, specific compositions and methods of providing a back brace have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A brace, comprising:
   a lumbar support that is adapted to provide support to a lumbar area of a wearer;
   a lateral support coupled to the lumbar support and having front and rear sides, wherein the lateral support has a loophole and a plurality of apertures each of which is sized and dimensioned to allow receipt of a connector;

a fitting belt coupled to the lumbar support via the lateral support, wherein the fitting belt includes the connector;

wherein the connector is configured to mate with at least one of the apertures, and wherein the fitting belt is configured to mate with a second fitting belt to adjust a length of the brace; and wherein the loophole is sized and dimensioned to allow the fitting belt to thread through the loophole when the connector of the fitting belt is coupled to the rear side of the lateral support and mated with at least one of the plurality of apertures.

2. The brace of claim 1, further comprising;

a joint on the lumbar support that couples rigid upper and lower sections of the lumbar support, wherein the rigid upper and lower sections of the lumbar support each support lumbar areas of the wearer;

wherein the lateral support is rigid such that the joint moves anteriorly on the wearer relative to the lateral support, wherein the joint is flexible relative to the upper and lower sections and to the lateral support, and wherein the upper section has separate right and left components coupled by an upper mechanically advantaged system.

3. The brace of claim 2, wherein the upper mechanically advantaged system comprises a cord and at least three pulleys that collectively operate to draw the right and left components towards one another.

4. The brace of claim 2, further comprising a limiter separate from the upper mechanically advantaged system that prevents the right and left components from moving a threshold distance away from one another, wherein the limiter is coupled to the lateral support.

5. The brace of claim 4, wherein the limiter comprises a compressible material.

6. The brace of claim 5, wherein the limiter comprises cloth.

7. The brace of claim 5, wherein the limiter includes a sagittal midplane hole.

8. The brace of claim 1, further comprising;

a joint on the lumbar support that couples rigid upper and lower sections of the lumbar support, wherein the rigid upper and lower sections of the lumbar support each support lumbar areas of the wearer;

wherein the lateral support is rigid such that the joint moves anteriorly on the wearer relative to the lateral support, wherein the joint is flexible relative to the upper and lower sections and to the lateral support, and a rigid panel that assists in preventing the flexible joint from bending, and is detachable from the brace.

9. The brace of claim 1, further comprising an extender that extends an effective height of the lumbar support.

10. The brace of claim 9, wherein the effective height is at least 10 inches.

11. The brace of claim 9, wherein the extender reinforces rigidity of the lumbar support.

12. The brace of claim 9, wherein the extender extends an effective width of the lateral support.

13. The brace of claim 12, further comprising a detachable support that further extends the effective width of the lateral support.

14. The brace of claim 1, wherein each of the plurality of apertures comprises opposing bolt recesses configured to allow receipt of the connector.

15. The brace of claim 1, further comprising:

the second fitting belt coupled to the lumbar support via a second lateral support disposed on an opposite side of the lumbar support, wherein the second fitting belt includes a second connector, and wherein the second fitting belt is configured to mate with the fitting belt;

wherein the second lateral support has front and rear sides, and wherein the second lateral support comprises (a) a second loophole and (b) a second plurality of apertures each of which is sized and dimensioned to allow receipt of the second connector; and wherein the second connector is configured to mate with at least one of the second plurality of apertures; and wherein the second loophole is sized and dimensioned to allow the second fitting belt to thread through the second loophole when the second fitting belt is coupled to the rear side of the second lateral support to further adjust the length of the brace.

* * * * *